US010206558B2

(12) United States Patent
Pfeiffer et al.

(10) Patent No.: US 10,206,558 B2
(45) Date of Patent: Feb. 19, 2019

(54) METHOD AND CAMERA FOR THE THREE-DIMENSIONAL MEASUREMENT OF A DENTAL OBJECT

(71) Applicant: SIRONA DENTAL SYSTEMS GMBH, Bensheim (DE)

(72) Inventors: Joachim Pfeiffer, Bensheim (DE); Frank Thiel, OberRamstadt (DE)

(73) Assignee: DENTSPLY SIRONA Inc., York, PA (US)

( * ) Notice: Subject to any disclaimer, the term of this patent is extended or adjusted under 35 U.S.C. 154(b) by 68 days.

(21) Appl. No.: 15/575,871

(22) PCT Filed: May 20, 2016

(86) PCT No.: PCT/EP2016/061370
§ 371 (c)(1),
(2) Date: Nov. 21, 2017

(87) PCT Pub. No.: WO2016/188881
PCT Pub. Date: Dec. 1, 2016

(65) Prior Publication Data
US 2018/0125338 A1 May 10, 2018

(30) Foreign Application Priority Data
May 22, 2015 (DE) .................. 10 2015 209 404

(51) Int. Cl.
*A61B 1/00* (2006.01)
*A61C 9/00* (2006.01)
(Continued)

(52) U.S. Cl.
CPC ...... *A61B 1/00172* (2013.01); *A61B 1/00188* (2013.01); *A61B 1/247* (2013.01);
(Continued)

(58) Field of Classification Search
CPC . A61B 1/00172; A61B 1/247; A61B 1/00188; A61C 9/0066; G01B 11/2513; G01B 11/2527; G02B 23/2415
See application file for complete search history.

(56) References Cited

U.S. PATENT DOCUMENTS 7,852,492 B2 * 12/2010 Berner ............... G01B 11/2513
356/605
8,577,212 B2 * 11/2013 Thiel ................... A61B 5/0068
348/46
(Continued)

*Primary Examiner* — Maurice Smith
(74) *Attorney, Agent, or Firm* — Dentsply Sirona Inc.

(57) ABSTRACT

The invention relates to a method and to a camera for the three-dimensional measurement of a dental object, comprising at least one light source, which emits an illumination beam, at least one projection means, which produces a projection pattern, focusing optics, which display the projection pattern in a plane of sharp focus at a defined focal distance relative to the dental camera. The projection pattern projected onto the object is reflected by the object as an observation beam and is acquired by means of a sensor. In the measurement of the object, the focusing optics are controlled in such a way that the focal distance of the plane of sharp focus relative to the camera is varied incrementally between a plurality of defined scan positions.

28 Claims, 3 Drawing Sheets

(51) Int. Cl.
*G01B 11/25* (2006.01)
*A61B 1/247* (2006.01)
(52) U.S. Cl.
CPC ............ *A61C 9/006* (2013.01); *A61C 9/0066* (2013.01); *G01B 11/25* (2013.01); *G01B 11/2513* (2013.01); *G01B 11/2527* (2013.01)

(56) References Cited

U.S. PATENT DOCUMENTS

| | | | |
|---|---|---|---|
| 2010/0189341 A1* | 7/2010 | Oota | A61B 1/0019 382/154 |
| 2015/0029309 A1* | 1/2015 | Michaeli | G02B 21/0028 348/46 |
| 2016/0231551 A1* | 8/2016 | Berner | A61C 9/006 |

* cited by examiner

METHOD AND CAMERA FOR THE THREE-DIMENSIONAL MEASUREMENT OF A DENTAL OBJECT

TECHNICAL FIELD

The invention relates to a method and a camera for the three-dimensional measurement of a dental object, comprising at least one light source which emits an illumination beam, at least one projection means, which produces a projection pattern, focusing optics, which display the projection pattern in a plane of sharp focus at a defined focal distance relative to the dental camera, wherein the projection pattern projected onto the object is reflected by the object as an observation beam and acquired by means of a sensor.

BACKGROUND OF THE INVENTION

A number of methods and cameras for the three-dimensional measurement of dental objects are known from the state of the art.

WO 2012/083967 A1 discloses a device for optical 3D measurement of an object using an optical confocal measurement method, wherein, in addition to a first light source, at least one second light source is used, the light of which is coupled into the beam path of the device using a light guide. It is furthermore disclosed that the light sources, such as color LEDs or LEDs in combination with color filters, can be used, whereby the light sources are switched on in an alternating manner to ensure homogeneous illumination.

WO 2010/145669 A1 discloses a device for optical 3D measurement of an object using an optical confocal measurement method. In this case, a temporally changing pattern is projected onto the object. The changing pattern is generated with the aid of a motor-driven mechanical means in the form of a wheel.

One disadvantage of these methods is that the temporally changing projection pattern is generated using movable projection means in the illumination beam path, such as a motor-driven, wheel-shaped projection grating. Incorrect control or incorrect actuation of the mechanically driven projection gratings can cause positioning errors, as a result of which incorrect three-dimensional image data of the object is obtained.

A further disadvantage is that the mechanically driven projection gratings require installation space, which results in an increase of the overall size of the camera.

The task of the present invention is therefore to provide a camera, which is of compact design and allows an error-free measurement of the dental object.

SUMMARY OF THE INVENTION

The invention relates to a camera for the three-dimensional measurement of a dental object, comprising at least one light source which emits an illumination beam, at least one projection means, which produces a projection pattern, focusing optics, which display the projection pattern in a plane of sharp focus at a defined focal distance relative to the dental camera, wherein the projection pattern projected onto the object is reflected by the object as an observation beam and acquired by means of a sensor. During the measurement of the object, the focusing optics are controlled in such a way that the focal distance of the plane of sharp focus relative to the camera is varied incrementally between a plurality of defined scan positions, wherein a first image and at least one second image are taken by means of the sensor for each scan position. In doing so, the sensor is moved back and forth in an oscillating manner laterally to the beam path of the observation beam, wherein the first image is acquired in a first sensor position of the sensor and the second image is acquired in a second sensor position of the sensor.

The camera can be integrated into a conventional housing in the form of a handpiece. The light source can be a single LED, or a group of LEDs, for example, that emits an illumination beam with a broad spectrum. The light source can therefore be a white LED or a combination of multiple colored LEDs. The light source can also be a laser LED or a laser diode, which emits a monochromatic illumination beam. The projection means can be a projection grating or a projection mask that produces the projection pattern. The projection means can also be a digital light projector made of liquid-crystal elements (LCD), which is controlled as appropriate and produces the projection pattern. The focusing optics are adjustable and focus the projection pattern onto the established plane of sharp focus, whereby the plane of sharp focus is varied incrementally so that the entire object is scanned. The scan positions can, for example, have a distance of 0.1 mm from one another. This distance therefore defines the resolution along a scan direction. The adjustment of the focusing optics can be carried out continuously, whereby only the image data of the images is read discretely at the defined scan positions.

The first image and at least the second image are generated for every scan position, whereby the sensor is moved back and forth in an oscillating manner. According to this method, therefore, the intensity and the change in intensity can be recorded for every pixel of the sensor. The difference between the intensity values in the first image and in the second image can thus be determined and from this, the contrast or sharpness of the two images. Based on a contrast value or sharpness, a focal distance of a surface of the object to be measured relative to the plane of sharp focus can then be determined. The reason for this is that, if the object surface to be measured deviates from the plane of sharp focus, the object will appear blurred in the images. If the focal distance of the plane of sharp focus or the focal length of the focusing optics is known, the distance of the object surface relative to the camera can be calculated.

A so-called depth-from-defocus measurement method (DfD), for example, can be used to determine the three-dimensional image data of the object. The images acquired in different focus positions are merged with one another to determine the three-dimensional image data of the object. For each pixel, for example, the intensity profile is plotted as a function of a frame number and thus as a function of the time and the focal position. If the object is not in the focal position, the contrast deteriorates. If the object is in the focal position, the contrast is at its maximum. The image with the maximum contrast is therefore acquired in the focal position of the camera. In this way, the distance of the object relative to the camera is determined.

One advantage of this camera is that, in comparison to mechanical projection means in the illumination beam path, the movement of the sensor makes a more compact design of the camera possible.

Another advantage of this camera is that the adjustment of the sensor between the two sensor positions can be controlled very precisely, which makes an error-free measurement of the object possible.

The projection pattern can advantageously be a checkerboard-like pattern and consist of dark and light square pattern elements.

The checkerboard-like pattern makes it possible to quickly change between dark and light pattern elements simply by shifting the sensor by one pattern element.

The projection means can advantageously be dimensioned and aligned in such a way that each pattern element of the projection pattern is projected onto one pixel of the sensor, so that the projected image of the pattern element in the plane of the sensor corresponds to the dimensions of the pixel.

One individual pattern element is thus projected onto one individual pixel, so that, during the oscillating movement of the sensor, a dark and a light pattern element is alternately projected onto each pixel. As a result, the difference between the two intensity values in the first image and in the second image can be easily determined for each pixel. If the surface of the object to be imaged is in the plane of sharp focus, the image of this pattern will be sharp, so that the difference in the intensity values, and thus the contrast, is at its maximum. The individual points of the object can thus be measured and this information can be used to generate the three-dimensional image data of the object.

During the oscillating movement, the sensor can advantageously be moved between the first sensor position and the second position sensor by a distance that corresponds to the width of a pixel of the sensor.

The movement of the sensor between the first sensor position and the second position sensor is thus minimally small and can be accomplished, for example, by means of a piezo element. The distance of the lateral movement can alternatively also correspond to a multiple of the width of the pixel.

Advantageously, the sensor can be moved along a first sensor axis parallel to the rows or along a second sensor axis parallel to the columns.

The adjustment of the sensor along the rows or along the columns can thus easily be performed.

The camera can advantageously comprise an observation mask in the beam path of the observation beam in front of the sensor, which is moved together with the sensor between the two sensor positions.

The observation mask can also comprise a checkerboard-like structure, for example, like the projection pattern.

The observation mask can advantageously be a Bayer filter, which comprises a checkerboard-like structure consisting of red, green and blue color filters, each of which is associated with one pixel of the sensor, so that a color measurement of the dental object is made possible.

A specific color filter is therefore placed in front of each pixel, so that the color of the object can be determined when evaluating the individual intensity values of the pixels.

The three-dimensional measurement and the color measurement can thus be carried out at the same time with a joint depth scan.

The different color filters can also have other colors that are suitable for performing a color measurement. A color filter can also be associated with a group of pixels of the sensor, such as a 2×2 or a 4×4 group of pixels.

Using the first image in the first sensor position and the second image in the second sensor position, which is offset by one pixel relative to the first sensor position, a first intensity value in the first sensor position and a second intensity value in the second sensor position can advantageously be determinable for every pixel of the sensor, wherein a difference value between the first intensity value and the second intensity value can be determinable by calculating the difference with the aid of an arithmetic unit of the camera.

The difference value between the two intensity values, which corresponds to a contrast value, is thus determined. The change in the difference value in the course of the adjustment between the individual scan positions can thus be determined, wherein the maximum of this difference value corresponds to the depth position of the surface of the object.

With the aid of the arithmetic unit and using the difference value as a function of the focal distance, depth information of an object surface of the object can advantageously be obtained for every pixel, thus generating three-dimensional surface data of the object.

The depth information for a plurality of measuring points of the object surface is thus determined, so that the three-dimensional surface data of the object can be generated from this information.

The projection pattern can advantageously consist of a plurality of parallel light and dark stripes.

As a result, a conventional projection pattern consisting of parallel stripes is used.

The projection means can advantageously be dimensioned and aligned in such a way that each stripe of the projection pattern is projected onto one column or one row of pixels of the sensor, so that the width of a projected stripe in the plane of the sensor corresponds to the width of the pixel.

Therefore, each stripe of the projection pattern is projected onto one column or one row of the sensor.

During the oscillating movement, the sensor can advantageously be displaced by a distance between the first sensor position and the second sensor position, which corresponds to the width of one pixel of the sensor, wherein the sensor is moved perpendicular to the projected stripes.

The oscillating movement of the sensor therefore displaces the sensor only by the width of one pixel, whereby a light stripe or a dark stripe of the projection pattern is alternately projected onto each pixel.

For a projection pattern of parallel stripes, the camera can advantageously comprise an observation mask in the beam path of the observation beam in front of the sensor, which is moved together with the sensor, whereby the observation mask is a Bayer filter consisting of a checkerboard-like structure of red, green and blue color filters, each of which is associated with one pixel of the sensor, so that a color measurement of the dental object is made possible.

The use of the Bayer filter therefore makes a color measurement possible in addition to the three-dimensional measurement of the object.

Using the first image in the first sensor position and the second image in the second sensor position, which is offset perpendicular to the stripes by one pixel relative to the first sensor position, a first intensity value in the first sensor position and a second intensity value in the second sensor position can advantageously be obtainable for every pixel of the sensor, wherein a difference value between the first intensity value and the second intensity value can be obtained by calculating the difference with the aid of an arithmetic unit of the camera, wherein with the aid of the arithmetic unit and using the difference value as a function of the focal distance, depth information of an object surface of the object is obtained for every pixel, thus making it possible to measure the three-dimensional surface data of the object.

The determination of the difference value as a measure of the change in the contrast is thus made possible in a simple manner. Therefore, when the change in the difference value is at its maximum, the plane of sharp focus lies within the object surface.

The sensor can advantageously be a CMOS sensor or a CCD sensor.

The conventional sensor types can therefore be used. A CMOS sensor would have the advantage that the individual images can be read more quickly.

The oscillating movement of the sensor can advantageously be carried out by means of an electric motor or by means of a piezo element with a frequency of at least 3,000 Hz.

A frequency of 6,000 Hz is obtained, for example, in a camera that comprises 300 scan positions per depth scan, wherein two images are taken in the two sensor positions in each scan position, wherein the images have an imaging time of 100 ms. For a smaller number of scan positions and for longer imaging times, the frequency can also be significantly lower; up to 100 Hz, for example.

A piezo element is particularly well suited to make a particularly quick and precise adjustment between the two scanning positions possible.

The invention further relates to a method for the three-dimensional measurement of a dental object by means of a camera, comprising at least one light source, which emits an illumination beam, at least one projection means which produces a projection pattern, focusing optics, which display the projection pattern in a plane of sharp focus at a defined focus distance relative to the dental camera, wherein the projection pattern projected onto the object is reflected by the object as an observation beam and acquired by means of a sensor. During the measurement of the object, the focusing optics are controlled in such a way that the focal distance of the plane of sharp focus relative to the camera is varied incrementally between a plurality of defined scan positions, wherein a first image and at least one second image are taken by means of the sensor for each scan position.

At least two images are therefore generated for every scan position to determine the contrast.

One advantage of this method is that a contrast or sharpness of the two images can easily be determined by comparing the two images. This information can then be used to determine the distance of the object from the camera, and thus the three-dimensional image data of the object.

The sensor can advantageously be moved back and forth in an oscillating manner laterally to the beam path of the observation beam, wherein the first image is acquired in a first sensor position of the sensor and the second image is acquired in a second sensor position of the sensor, wherein, during the oscillating movement, the sensor is moved along a first sensor axis parallel to the rows of the sensor pixels or along a second sensor axis parallel to the columns of the sensor pixels by a distance between the first sensor position and the second sensor position, which corresponds to the width of a pixel of the sensor.

As a result of the movement of the sensor, each pixel is alternately illuminated with a light pattern element or a dark pattern element of the projection pattern. The difference value, and with it the contrast, can thus be determined by the time dependence of the intensities of each pixel.

The projection means can advantageously be moved back and forth in an oscillating manner laterally to the beam path of the illumination beam, wherein the first image is acquired in a first position of the projection means and the second image is acquired in a second position of the projection means, wherein, during the oscillating movement, the projection means is moved along a first sensor axis parallel to the rows or along a second sensor axis parallel to the columns by a distance, which is dimensioned in such a way that the projection pattern is moved in the plane of the sensor by the width of a pixel of the sensor.

The change in the projection pattern is thus produced by the oscillating movement of the projection means.

The projection pattern can advantageously be a checker-board-like pattern and consist of dark and light square pattern elements.

As a result, when the projection pattern is displaced by one pixel, a light or a dark pattern element is alternately projected onto each pixel of the sensor.

The projection means can advantageously be dimensioned and aligned in such a way that each pattern element of the projection pattern is projected onto one pixel of the sensor, so that the projected image of the pattern element in the plane of the sensor corresponds to the dimensions of the pixel.

The movement of the projection means is therefore minimal and can be ensured by means of a compact and precise drive, such as a piezo element.

The camera can advantageously comprise an observation mask in the beam path of the observation beam in front of the sensor, which is moved together with the sensor, so that the dimensions of an image of a pattern element of the projection pattern in the plane of the observation mask correspond to the dimensions of an observation mask element.

In terms of its structure, the observation mask thus corresponds to the projection pattern.

The projection pattern can advantageously consist of a plurality of parallel stripes.

A conventional projection grating with parallel stripes, for example, can therefore be used to generate the projection pattern.

The projection means can advantageously be dimensioned and aligned in such a way that each stripe of the projection pattern is projected onto one column or one row of pixels of the sensor, so that the width of a projected stripe in the plane of the sensor corresponds to the width of the pixel, whereby the sensor or the projection means is moved perpendicular to the projected stripes.

By displacing the projection pattern by one pixel width, a light or a dark stripe is thus alternately projected onto each pixel of the sensor.

Advantageously, when using the first image in the first sensor position or in the first position of the projection means and the second image in the second sensor position or in the second position of the projection means, which is offset by one pixel relative to the first sensor position, for every pixel of the sensor a first intensity value can be obtained in the first sensor position or in the first position of the projection means and a second intensity value can be obtained in the second sensor position or in the second position of the projection means, wherein a difference value between the first intensity value and the second intensity value is obtained by calculating the difference with the aid of an arithmetic unit of the camera.

The difference value as a measure of the contrast can thus easily be determined by shifting the stripe pattern.

With the aid of the arithmetic unit and using the difference value as a function of the focal distance, depth information of an object surface of the object can advantageously be obtained for every pixel, thus generating three-dimensional surface data of the object.

The difference value as a function of the focal distance is thus obtained for every pixel, whereby the maximum of the difference value corresponds to the position of the object surface.

The camera can advantageously comprise an observation mask in the beam path of the observation beam in front of the sensor, which is moved together with the sensor, whereby the observation mask is a Bayer filter consisting of a checkerboard-like structure of red, green and blue color filters, each of which is associated with one pixel of the sensor, so that a color measurement of the dental object is made possible.

A color measurement of the object, in addition to the three-dimensional measurement of the object, is thus made possible. A square group of four can consist of two blue, one green and one red color filter, for example.

The oscillating movement of the sensor or the projection means can advantageously be carried out by means of an electric motor or by means of a piezo element with a frequency of at least 6,000 Hz.

BRIEF DESCRIPTION OF THE DRAWINGS

The invention is explained with reference to the drawings.

DETAILED DESCRIPTION OF THE INVENTION

Figure 1:
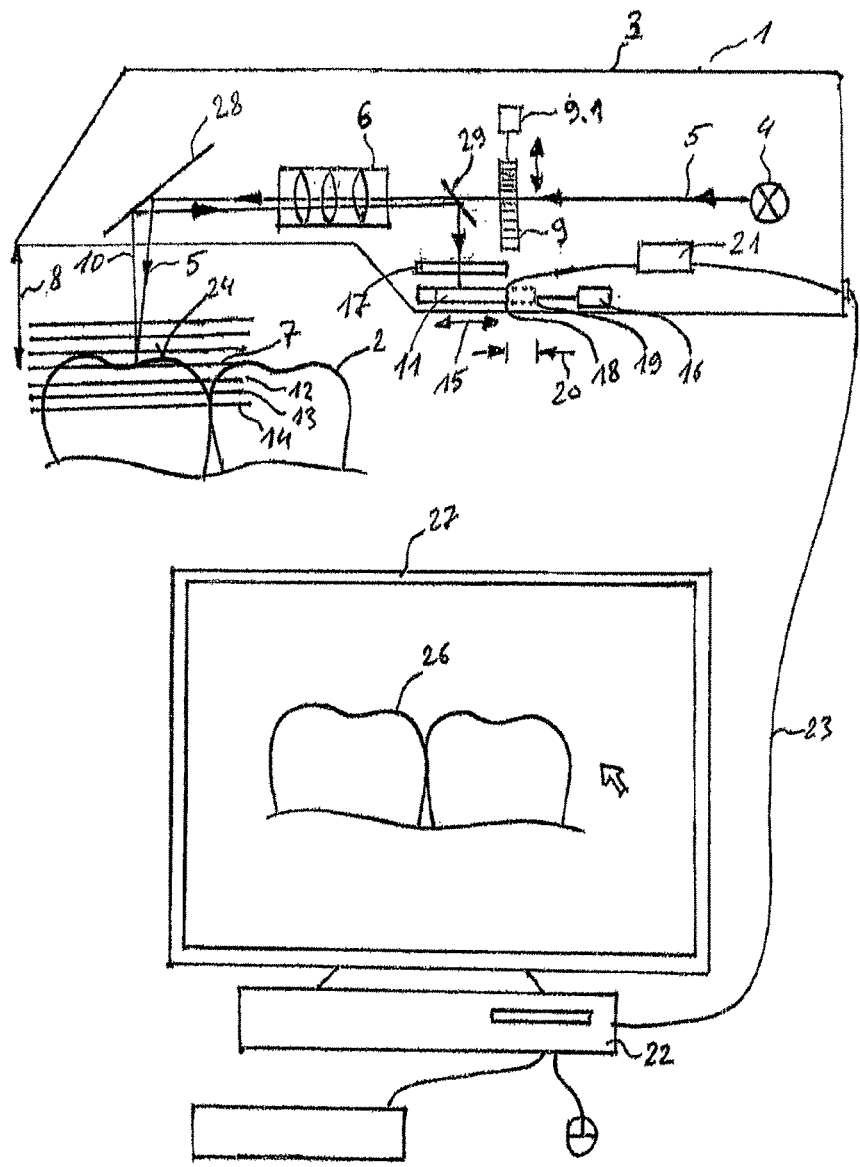
FIG. 1 shows a sketch of a camera for three-dimensional measurement.

FIG. 1 shows a sketch of a camera 1 for the three-dimensional measurement of a dental object 2, such as the depicted teeth of a patient, whereby the camera 1 is integrated in a housing 3 in the form of a handpiece. The camera comprises a light source 4 that emits an illumination beam 5, focusing optics for focusing the illumination beam 5 onto a plane of sharp focus 7 at a defined focal distance 8 relative to the camera 1. The camera 1 further comprises a projection means 9, such as a projection grating or an LCD light projector, for the purpose of producing a projection pattern. The projection pattern can comprise a checkerboard-like form, for example, or consist of several parallel stripes. The projection pattern is thus projected onto the object 2, reflected by the object 2 as an observation beam 10 and acquired by means of a sensor 11. When measuring the object 2, the focusing optics 6, which may for example consist of a plurality of lenses, is controlled in such a way that the focal distance 8 of the plane of sharp focus 7 relative to the camera 2 is adjusted incrementally between a plurality of defined scan positions 12, 13 and 14. A first image and at least one second image is generated for every scan position 7, 12, 13 or 14, whereby the sensor 11 is moved laterally to the beam path of the observation beam 10, as indicated by the arrow 15, with the aid of a drive means 16, such as a motor or a piezo element. As a result of the oscillating movement of the sensor 11, in each scan position 12, 13 and 14 every pixel of the sensor 11 is illuminated in an alternating manner with a light or a dark pattern element of the projection pattern. The scan positions 7, 12, 13 and 14 can, for example, be disposed at a distance of 0.1 mm from one another. The resolution in the Z-direction parallel to the observation beam 10 is thus defined by this distance between the scan positions. The camera additionally comprises an observation mask 17, which can be designed in the form of a Bayer filter made of a plurality of color filters, for example. In addition to the three-dimensional measurement of the object 2, such a Bayer filter 17 also allows a color measurement of the object 2. In the course of the movement 15 of the sensor 11, the sensor 11 is shifted between a first sensor position 18 and a second sensor position 19, shown as a dotted line, by a distance 20. This distance 20 can correspond to the width of a pixel of the sensor 11, for example. For every pixel of the sensor 11, therefore, a first intensity value is determined in the first sensor position 18 and a second intensity value is determined in the second sensor position 19, whereby a difference value between the first intensity value and the second intensity value is obtained by calculating the difference with the aid of an arithmetic unit 21. The observation mask 17 can be moved between the two sensor positions 18 and 19 along with the sensor 11, for example.

The arithmetic unit 21 can be a microcomputer or a chip, for example, that is integrated in the camera 1. The determination of the difference value can alternatively be performed with the aid of a computer 22, whereby the image data of the sensor 11 is transmitted to the computer by means of a cable connection 23 or wirelessly. In this manner, therefore, a difference value is determined for every pixel and for every scan position 7, 12, 13 or 14, whereby the difference value is at the maximum if the sharp layer 7 coincides with a surface 24 of the object 2. Otherwise, the projection pattern will be blurred on the surface 24 of the object 2. The image data of the sensor 11 is thus read after each image, as illustrated by the arrow 25, and transmitted to the computer. After the completed measurement of the object 2, the individual coordinates of the measuring points on the surface 24 of the measurement object 2 are used to calculate three-dimensional image data 26 of the object 2, which can be visualized by means of a display device 27, such as a monitor. As an alternative to moving the sensor 11, the projection means 9 can be actuated by using a second drive means 9.1, such as an electric motor or a piezo element. The control of the projection means 9 is then performed in such a way that the projection pattern is shifted in the plane of the sensor 11 by the width of one pixel, as indicated by the arrow. In another alternative, the sensor 11 and the projection means 9 can be moved synchronously to create the desired displacement of the projection pattern relative to the sensor 11. The camera 1 comprises a beam deflector 28, such as a mirror, which deflects the illumination beam 5 to the object 2. The camera 1 furthermore comprises a beam splitter 29, which deflects the observation beam 10 to the sensor 11. The focusing optics 6 are irradiated by both the illumination beam 5 and the observation beam 10.

Figures 2, 3:
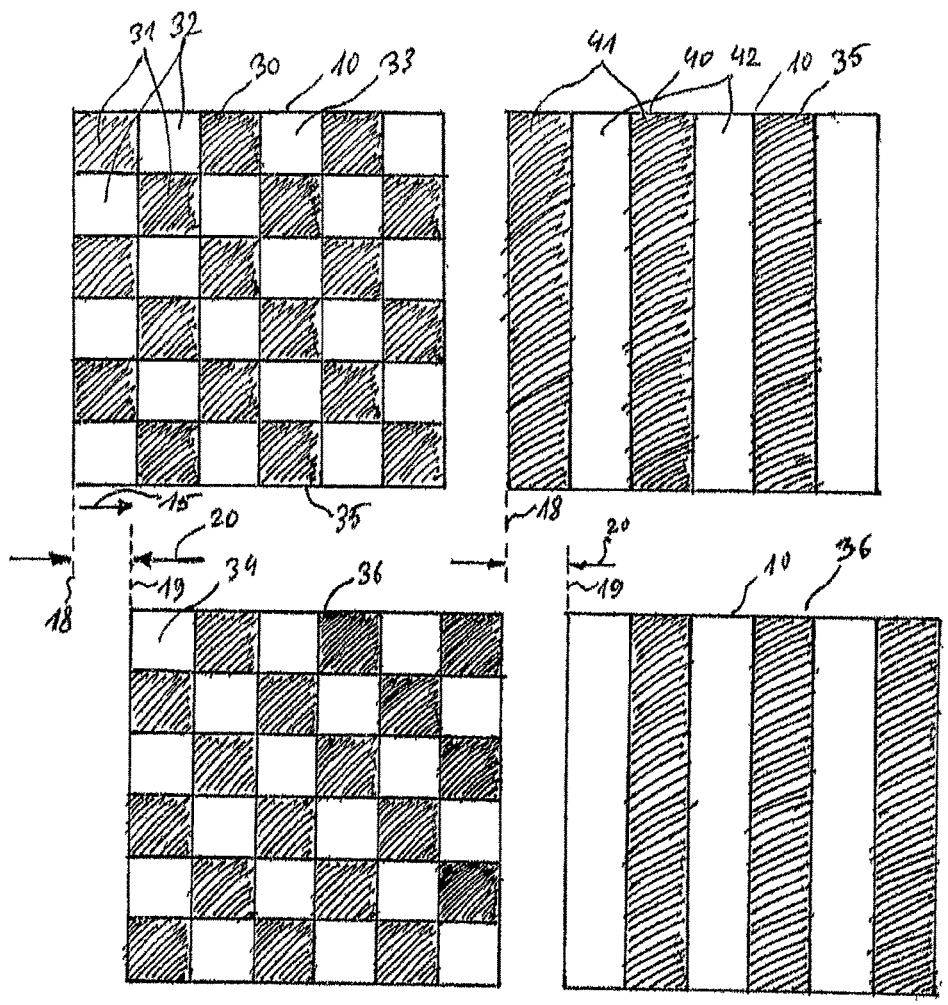
FIG. 2 shows a sketch of a checkerboard-like projection patter.
FIG. 3 shows a sketch of a projection pattern that consists of dark stripes and light stripes.

FIG. 2 shows a sketch of a checkerboard-like projection pattern 30 on the sensor 11 in the first sensor position 18. In their dimensions, the dark pattern elements 31 of the projection pattern 30 and the light pattern elements 32 of the projection pattern 30 correspond to the individual pixels 33 of the sensor 11. Due to the lateral displacement 15 by the distance 20, which corresponds to the width of one pixel 33, the pixel 34 in the upper left corner, for example, is illuminated with a light pattern element 32. In this way, each pixel of the sensor 11 is alternately illuminated with a light pattern element 32 or a dark pattern element 31. A difference value of the two intensity values from the first image 35 in the sensor position 18 and from the second image 36 in the second sensor position 19 can thus be obtained for each pixel. If the sharp layer coincides with the object surface 24 of the object, the image of the projection pattern 30 on the sensor 11 is in sharp focus, so that the individual difference values are at the maximum.

FIG. 3 shows a sketch of a projection pattern 40 that consists of dark stripes 41 and light stripes 42. As in FIG. 2, the projection pattern is shifted between the first sensor position 18 and the second sensor position 19 by the distance 20, which corresponds to one pixel width. As a result of this displacement of the sensor 11, every pixel of the sensor 11 is likewise alternately illuminated with a light stripe 42 or a dark stripe 41.

Figure 4:
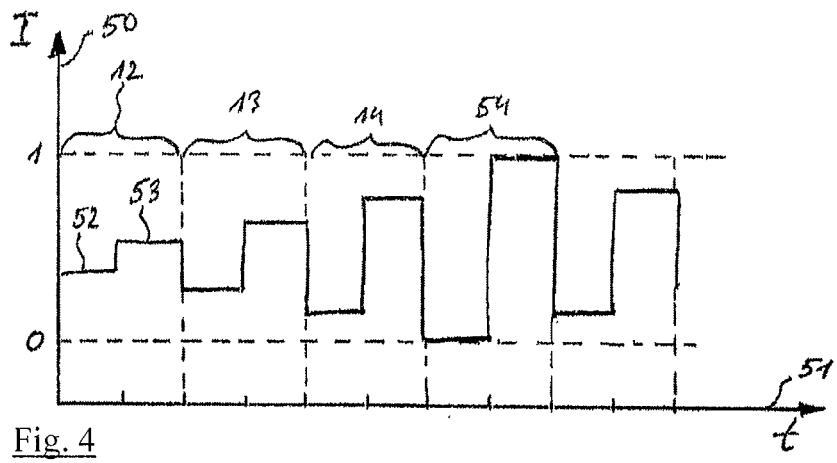
FIG. 4 shows a diagram of an intensity value as a function of the time.

FIG. 4 shows a diagram of an intensity value 50 on the y-axis as a function of the time 51 on the x-axis. In a first scan position 12, a first intensity value 52 on a scale between 0 and 1 is obtained from the first image 35 in the first sensor position 18 and a second intensity value 53 is obtained from the second image 36 in the second sensor position 19. The intensity values for a second scan position 13, a third scan position 14 and a fifth scan position 54 are obtained in the same manner.

Figure 5:
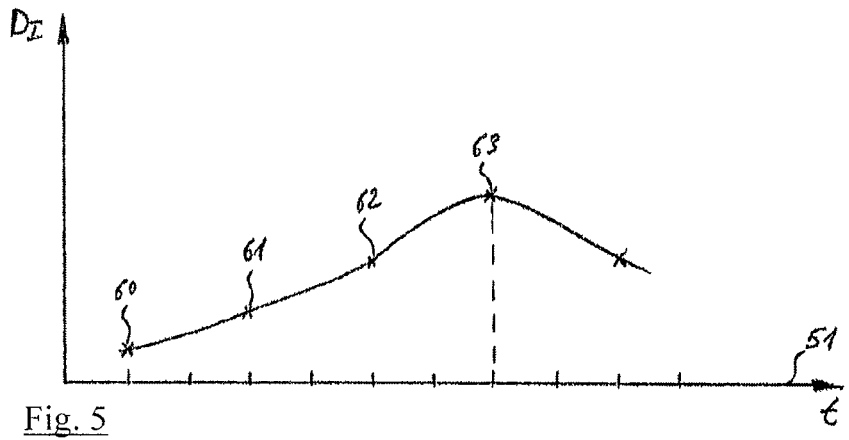
FIG. 5 shows a diagram of a difference value as a function of the time.

FIG. 5 shows a diagram to illustrate the present method, wherein a first difference value 60 for the first scan position 12, a second difference value 61 for the second scan position 13, a third difference value 62 for the third scan position 14 and a fourth difference value 63 for the fourth scan position 54 are obtained from the intensity value 52 and 53 by calculating the difference. The difference values are plotted as a function of the time 51. In the fourth scan position 54, the difference value 63 is at the maximum, so that in this scan position 54 the plane of sharp focus 7 coincides with the surface 24 of the object. Depth information of the corresponding measuring point on the surface 24 of the object can thus be obtained for every pixel.

Figure 6:
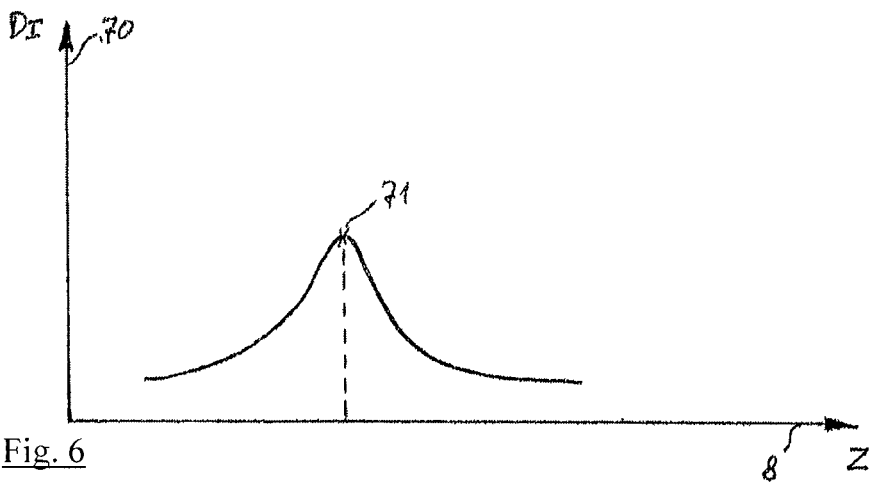
FIG. 6 shows a diagram of the difference value as a function of a focal distance.

FIG. 6 shows the difference value 70 as a function of the focal distance 8 for one individual pixel of the sensor 11. At a maximum 71 of the difference value, the contrast is at the maximum, because the image of the projection pattern 30 of FIG. 2 is in sharp focus.

REFERENCE SIGNS 1 camera
2 object
3 housing
4 light source
5 illumination beam
6 focusing optics
7 plane of sharp focus
8 focal distance
9 projection means
9.1 drive means
10 observation beam
11 sensor
12 scan position
13 scan position
14 scan position
15 arrow
16 drive means
17 observation mask/Bayer filter
18 sensor position
19 sensor position
20 distance
21 arithmetic unit
22 computer
23 cable connection
24 surface
25 arrow
26 image data
27 display device
28 mirror
29 beam splitter
30 projection pattern
31 pattern element
32 pattern element
33 pixels
34 pixels
35 first image
36 second image
40 projection pattern
41 dark stripes
42 light stripes
50 intensity value
51 time
52 intensity value
53 intensity value
54 scan position
60 first difference value
61 second difference value
62 third difference value
63 fourth difference value
70 difference value
71 maximum

The invention claimed is:

1. A camera for the three-dimensional measurement of a dental object, comprising:
   at least one light source, which emits an illumination beam,
   at least one projection means, which produces a projection pattern, and
   focusing optics, which display the projection pattern in a plane of sharp focus at a defined focal distance relative to the camera,
   wherein the projection pattern projected onto the object is reflected by the object as an observation beam and acquired by means of a sensor,
   wherein, during the measurement of the object, the focusing optics is controlled so that the focal distance of the plane of sharp focus relative to the camera is varied incrementally between a plurality of defined scan positions,
   wherein a first image and at least one second image are taken by means of the sensor for each scan position,
   wherein the sensor is configured to be moved back and forth in an oscillating manner laterally to the beam path of the observation beam,
   wherein the first image is acquired in a first sensor position of the sensor and the second image is acquired in a second sensor position of the sensor.

2. The camera according to claim 1, wherein the projection pattern is a checkerboard-like pattern consisting of dark and light square pattern elements.

3. Camera according to claim 2, wherein the projection means is dimensioned and aligned so that that every pattern element of the projection pattern is projected onto one pixel of the sensor, so that the projected image of the pattern element in the plane of the sensor corresponds to the dimensions of the pixel.

4. The camera according to claim 3, wherein, during the oscillating movement, the sensor is moved by a distance between the first sensor position and the second sensor position, which corresponds to the width of one pixel of the sensor.

5. The camera according to claim 4, wherein the sensor is moved along a first sensor axis parallel to the rows or along a second sensor axis parallel to the columns.

6. The camera according to claim 1, wherein the camera comprises an observation mask in the beam path of the observation beam in front of the sensor, which is moved together with the sensor between the two sensor positions.

7. The camera according to claim 6, wherein the observation mask is a Bayer filter that includes a checkerboard-like structure of red, green and blue color filters, each of which is associated with one pixel of the sensor so that a color measurement of the dental object is made possible.

8. The camera according to claim 1, wherein, when using the first image in the first sensor position and the second image in the second sensor position, which is offset by one pixel relative to the first sensor position, for every pixel of the sensor a first intensity value is obtained in the first sensor position and a second intensity value is obtained in the second sensor position, wherein a difference value between the first intensity value and the second intensity value is obtained by calculating the difference with the aid of an arithmetic unit of the camera.

9. The camera according to claim 8, wherein, with the aid of the arithmetic unit and using the difference value as a function of the focal distance, depth information of an object surface of the object is obtained for every pixel, thus making it possible to measure the three-dimensional surface data of the object.

10. The camera according to claim 1, wherein the projection pattern includes a plurality of parallel light and dark stripes.

11. The camera according to claim 10, wherein the projection means is dimensioned and aligned so that every stripe of the projection pattern is projected onto a column or a row of pixels of the sensor, so that the width of a projected stripe in the plane of the sensor corresponds to the width of the pixel.

12. The camera according to claim 11, wherein, during the oscillating movement, the sensor is moved by a distance between the first sensor position and the second sensor position that corresponds to the width of one pixel of the sensor, wherein the sensor is moved perpendicular to the projected stripes.

13. The camera according to claim 10, wherein the camera comprises an observation mask in the beam path of the observation beam in front of the sensor, wherein the observation mask is a Bayer filter, which comprises a checkerboard-like structure of red, green and blue color filters, each of which is associated with one pixel of the sensor, thus making a color measurement of the dental object possible.

14. The camera according to claim 10, wherein, when using the first image in the first sensor position and the second image in the second sensor position, which is offset perpendicular to the stripes by one pixel relative to the first sensor position, for every pixel of the sensor a first intensity value is obtained in the first sensor position and a second intensity value is obtained in the second sensor position, wherein a difference value between the first intensity value and the second intensity value is obtained by calculating the difference with the aid of an arithmetic unit of the camera, wherein, with the aid of the arithmetic unit and using the difference value as a function of the focal distance, depth information of an object surface of the object is obtained for every pixel, thus making it possible to measure the three-dimensional surface data of the object.

15. The camera according to claim 1, wherein the sensor is a CMOS sensor or a CCD sensor.

16. The camera according to claim 1, wherein the oscillating movement of the sensor is carried out by means of an electric motor or by means of a piezo element with a frequency of at least 6,000 Hz.

17. A method for three-dimensional measurement of a dental object using a camera comprising:
emitting an illumination beam from at least one light source,
producing a projection pattern from at least one projection means,
displaying the projection pattern in a plane of sharp focus at a defined focal distance relative to the camera using focusing optics,
reflecting as an observation beam the projection pattern projected onto the dental object,
acquiring said reflected projection pattern using a sensor,
controlling the focusing optics such that the focal distance of the plane of sharp focus relative to the camera is varied incrementally between a plurality of defined scan positions,
taking a first image and at least one second image by means of the sensor
moving the sensor back and forth in an oscillating manner laterally to the beam path of the observation beam,
acquiring the first image in a first sensor position and the second image in a second sensor position.

18. The method according to claim 17 further comprising:
moving, during the oscillating movement, the sensor along a first sensor axis parallel to the rows of the sensor pixels or along a second sensor axis parallel to the columns of the sensor pixels by a distance between the first sensor position and the second sensor position, which corresponds to the width of a pixel of the sensor.

19. The method according to claim 17 further comprising:
moving the projection means back and forth in an oscillating manner laterally to the beam path of the illumination beam,
acquiring the first image in a first position of the projection means and the second image in a second position of the projection means,
moving, during the oscillating movement, the projection means along a first sensor axis parallel to the rows or along a second sensor axis parallel to the columns by a distance,
wherein said distance is dimensioned in such a way that the projection pattern is moved in the plane of the sensor by the width of a pixel of the sensor.

20. The method according to claim 17, wherein the projection pattern is a checkerboard-like pattern of dark and light and square pattern elements.

21. The method according to claim 20, wherein the projection means is dimensioned and aligned in such a way that every pattern element of the projection pattern is projected onto one pixel of the sensor, so that the projected image of the pattern element in the plane of the sensor corresponds to the dimensions of the pixel.

22. The method according to claim 21, wherein the camera comprises an observation mask in the beam path of the observation beam in front of the sensor, so that the dimensions of an image of a pattern element of the projection pattern in the plane of the observation mask correspond to the dimensions of an observation mask element.

23. The method according to claim 17, wherein the projection pattern includes a plurality of parallel stripes.

24. The method according to claim 23, further comprising:

Dimensioning and aligning the projection means such that each stripe of the projection pattern is projected onto one column or one row of pixels of the sensor, so that the width of a projected stripe in the plane of the sensor corresponds to the width of the pixel, wherein the sensor or the projection means is moved perpendicular to the projected stripes.

25. The method according to claim 18, wherein, when using the first image in the first sensor position or in the first position of the projection means and the second image in the second sensor position or in the second position of the projection means, which is offset by one pixel relative to the first sensor position, for every pixel of the sensor a first intensity value is obtained in the first sensor position or in the first position of the projection means and a second intensity value is obtained in the second sensor position or in the second position of the projection means, wherein a difference value between the first intensity value and the second intensity value is obtained by calculating the difference with the aid of an arithmetic unit of the camera.

26. The method according to claim 25, wherein, with the aid of the arithmetic unit and using the difference value as a function of the focal distance, depth information of an object surface of the object is obtained for every pixel, thereby generating three-dimensional surface data of the object.

27. The method according to claim 17, wherein the camera comprises an observation mask in the beam path of the observation beam in front of the sensor, wherein the observation mask is a Bayer filter consisting of a checkerboard-like structure of red, green and blue color filters, each of which is associated with one pixel of the sensor so that a color measurement of the dental object is made possible.

28. The method according to claim 17, further comprising:
carrying out the oscillating movement of the sensor or the projection means by means of an electric motor or by means of a piezo element with a frequency of at least 6,000 Hz.

* * * * *